United States Patent [19]

Amselem

[11] 4,018,786
[45] Apr. 19, 1977

[54] 2-AMINOTHIAZOLINES AND A PROCESS FOR PREPARATION THEREOF

[75] Inventor: Armand Amselem, Toulouse, France

[73] Assignee: Centre d'Etudes pour l'Industrie Pharmaceutique, Toulouse, France

[22] Filed: Aug. 6, 1974

[21] Appl. No.: 495,214

[52] U.S. Cl. .................. 260/306.7 T; 260/240 R; 424/270

[51] Int. Cl.² .................................. C07D 277/42

[58] Field of Search .......................... 260/306.7 T

[56] References Cited

FOREIGN PATENTS OR APPLICATIONS

| 814,579 | 5/1974 | Belgium | 260/307 T |
|---|---|---|---|
| 2,247,234 | 5/1975 | France | 260/307 T |

Primary Examiner—Donald G. Daus
Assistant Examiner—D. B. Springer
Attorney, Agent, or Firm—Cushman, Darby & Cushman

[57] ABSTRACT

Amino-2 thiazoles of the formulae

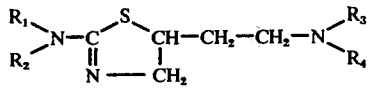

and

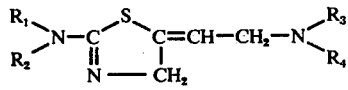

wherein $R_1$ and $R_2$ are each selected from hydrogen, lower alkenyl radicals, lower alkyl radicals, lower cycloalkyl radicals, phenyl radical, lower cycloalkylphenyl radicals, lower phenylalkyl radicals, lower halogenoalkenyl radicals, lower halogenoalkyl radicals, lower halogenocycloalkyl radicals, halogenophenyl radicals, lower halogenoalkyl radicals, and the same radicals substituted by at least a hydroxy, $R_3$ and $R_4$ are each selected from hydrogen, lower alkyl and lower cycloalkyl, one at least of $R_1$ and $R_2$ being cyclic, and their salts, have valuable hypocholesterolemic activity.

6 Claims, No Drawings

2-AMINOTHIAZOLINES AND A PROCESS FOR PREPARATION THEREOF

The present invention relates to new derivatives of 2-aminothiazole, to a process for preparation thereof and to the use thereof in human and veterinary medicine.

The compounds according to the invention are of the formula:

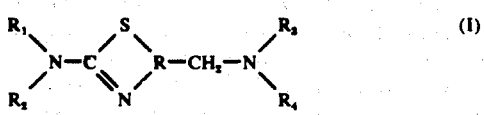

wherein R is a group of formula:

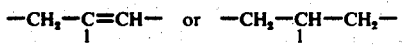

linked with the sulphur atom by its second carbon atom; $R_1$ and $R_2$, which may be the same or different, are hydrogen atoms or, alkenyl, alkyl, cycloalkyl, aryl or aralkyl groups (which groups may optionally be substituted by halogen atoms or hydroxy groups) or form, together with the nitrogen atom to which they linked, a saturated heterocyclic ring having 4 to 8 ring members and optionally containing a nitrogen, oxygen, or sulphur atom as a second heteroatom and being optionally substituted by an alkyl group; and $R_3$ and $R_4$, which may be the same or different, are hydrogen atoms, alkyl or cycloalkyl groups, or form, together with the nitrogen atom to which they are linked, a saturated heterocyclic ring having 5 or 6 ring members and optionally containing oxygen, nitrogen, or sulphur as a second heteroatom which (in the case of nitrogen) is optionally substituted by an aryl (preferably phenyl) group, (which itself is optionally substituted by a halogen atom) or an alkyl, hydroxyalkyl, haloalkyl, alkoxy, trifluoromethyl or halohydroxyalkyl group.

The alkyl and alkenyl groups and the alkyl portions of the aralkyl groups in the compounds of the formula I advantageously are straight or branched and have 1 to 12 carbon atoms, and preferably 1 to 4 carbon atoms in their straight chain.

When $R_1$ or $R_2$ are aryl or aralkyl, the aryl group is preferably phenyl, whilst the cycloalkyl groups in the derivatives of formula (I) generally have 4 to 12 carbon atoms, and particularly 5 to 8 carbon atoms, in the ring.

The derivatives (I) possess valuable anti-inflammatory and hypocholesterolemic properties.

These properties, associated with a low toxicity, are particularly marked in the case of the compounds of formula (I) comprising two heterocyclic rings and especially a heterocyclic ring containing two nitrogen atoms one of which carries an alkyl group. Compounds wherein $R_1$ is cycloalkyl are also important.

Compounds of the formula I may be prepared by reacting an amine of the formula AH with an isothiocyanate of the formula $B - N = C = S$ (A being $-N(R_1R_2)$ when B is $-CH_2-R_o-CH_2-N(R_3R_4)$ and, when $R_2$ is hydrogen, being $N(R_3R_4)-CH_2-R_o-CH_2-NH-$ when B is $R_1 -$, $R_o$ being a vinylene group ($-CH=CH-$) or ethynylene ($-C \equiv C-$) group) to form an intermediate of formula:

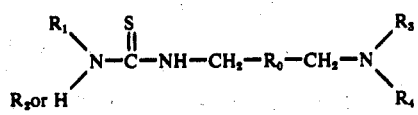

then cyclising this intermediate, by heating in acid medium, to form a thiazoline derivative of formula:

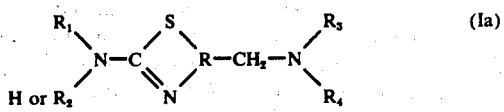

wherein R is the saturated trivalent group, when $R_o$ is vinylene, or is the unsaturated trivalent group linked to the nitrogen atom by its carbon atom which is not adjacent to its double bond, when $R_o$ is ethynylene; and, in preparing the thiazole derivative of formula I wherein R is linked to the nitrogen atom by its carbon atom adjacent to its double bond, isomerising the compound of the formula Ia wherein R has a double bond.

The starting amines $N(R_3R_4) - CH_2-R_o-CH_2-NH_2$ are known compounds and may be prepared by the process described by R. Dahlbom, B. Karlen, A. Lindquist, R. George and D. J. Jenden in Acta Pharm. Suedica, 4, (4) 247, (1967) or in Chem. Abst. 68,21805 k (1968) when $R_o$ is ethynylene. When $R_o$ is vinylene, they may be prepared by the process of T. Singh, R. Stiel and J. Biel in J. Med. Chem., 1969,12,368.

The preparation of the new starting isothiocyanates $N(R_3R_4)-CH_2-R_o-CH_2-N=C=S$ may be effected in conventional manner by treating an amine of the formula $N(R_3R_4)-CH_2-R_o-CH_2-NH_2$ with carbon disulphide in the presence of cyclohexylcarbodiimide, at a low temperature (e.g. $-20°$ to $-10°$ C) in a solvent such as ether.

The reaction of the amine AH with the isothiocyanate $B = M = S$ is generally performed by admixing solutions containing stoichiometric quantities of the two reagents, the solvent being the same for each solution (eg. hydrocarbon), for example under reflux for 15 minutes to three hours according to the nature of A and of B, evaporating of the solvent under vacuum, dissolving the residue, which is generally oily, in an aqueous acid solution, heating this solution to 100° C for at least above 1 hour, cooling and separating the precipitate or the oily phase which is formed by adding alkali.

The precipitate can be isomerised by heating it to reflux in a solvent with high boiling point, for example higher than 100° C, or by treating it with a concentrated acid, such as concentrated sulphuric acid, at about 80° C for period of time varying from a few minutes to a few hours.

The compound of the formule I may be prepared in the form of their simple or multiple acid addition salts with mineral or organic acids, such as their hydrohalides, for example their hydrochlorides, hydrobromides, sulphates, oxalates, methanesulphonates, maleates, lactates, or tartrates, or in the form of quaternary ammonium salts. These salts are prepared by dissolving the free base in etherified solutions containing a stoichiometric quantity of the chosen acid.

The following examples illustrate the invention.

EXAMPLE 1

Preparation of 2-cyclohexylamino 5-β-diethylaminoethylidene Δ²-thiazoline (derivative No.1) and of its hydrochloride $R_1$ = cyclohexyl; $R_2$ = H; $R_3$ = solution $R_4$ = ethyl.

a. Into a solution of 21g (0.15 mole) of 1-amino 4-diethylamino 2-butyne in 50 ml of benzene is introduced, dropwise, a solution of 21g (0.15 mole) of cyclohexyl isothiocyanate in 50 ml of benzene.

The mixture is heated to reflux for 40 minutes, then the benzene is evaporated under vacuum. The residual oil is taken up in 150 ml of 2N HCL and the mixture is heated for 1 hour at 100° C. After cooling, the reaction medium is neutralised by addition of a solution of 2N NaOH. The precipitate formed is filtered and dried. Thus there is obtained 38.2 g of the crude product (yield, 90%), which, after purification, by recrystallisation in an ether mixture of petroleum/cyclohexane, provides 29g of crystals (yield 70%) whose melting point, determined by Koefler block, is 125°–126° C.

b. In a flask containing 8.25g (0.14 mole) of dicyclohexylcarbodiimide, 30ml of carbon disulphide and 100 ml of ether is introduced, dropwise, solution of 5.6g (0.04 mole) of 1-amino 4-diethyl-amino 2-butyne in 5 ml of the same solvent. The temperature of the mixture is kept between −10° and −12° C during the introduction of the amine, then the mixture is left at ambient temperature for 18 hours. After filtering, the etherified solution is evaporated under vacuum. The oily residue constituted by 4-diethylamino 1-isothiocyanato 2-butyne, is dissolved in 25 ml of benezene, then introduced into a mixture of 3.96g (0.04 mole) of cyclohexylamine dissolved in 25 ml of the same solvent.

The mixture is heated to reflux for 40 minutes, then the benzene is evaporated under vacuum. The residual oil is taken up in a solution of 2N HCL and the mixture is heated for 1 hour at 100° C. After cooling, the reaction medium is neutralised by addition of a solution of 2N NaOH. The precipitate formed is filtered, dried, then recrystallised from an ether mixture of petroleum and cyclohexane. Thus there is obtained, in a yield of 43%, 4.8g of crystals identical to those obtained previously.

c. The precipitate obtained previously in the crude state is dissolved in ether. To the solution is added ether saturated with hydrochloric acid. The hydrochloride precipitated is collected and recrystallised from a mixture of isopropanol and isopropyl ether. Crystals are obtained whose melting point, determined by Koefler block, is 225° C.

EXAMPLE 2

Preparation of 2-cyclohexylamino 5-β-diethylaminoethyl thiazole (derivative No. 2, thiazole isomer of derivative No. 1).

A solution of 6g of the derivative No. 1 in 100 ml of a mixture consisting of 4 volumes of glacial acetic acid to one volume of 40% aqueous hydrobromic acid is heated to reflux for 16 hours. The cooled solution is neutralised with an aqueous solution of 2N NaOH, then extracted with ether. The organic phase is separated, washed with water, dried over $Na_2SO_4$ and then evaporated. 5.6g are obtained of a crude product (yield 93%) which, after recrystallisation from petroleum ether, results in crystals whose melting point is 89°–90° C.

By treatment with a solution of hydrochloric acid in ether, a dihydrochloride is obtained whose melting point is 190° C.

EXAMPLE 3

Preparation of 2-cyclohexlamino 5-β-diethylaminoethyl Δ²-thiazoline (derivative No. 3).

While maintaining the temperature at between 5° and 10° a solution of 7.05g(0.05 mole) of cylcohexyl isothiocyante in 25ml of benzene is mixed with a solution of 7.1g(0.05 mole) of 1-amino 4-diethylamino 2-butene in 25 ml of the same solvent. After 2 hours the benzene is evaporated and 14g of a residual oil are recovered which is dissolved in a mixture of 4 volumes of glacial acetic acid to 1 volume of a 40% aqueous solution of H Br.

The mixture is heated for 15 hours under reflux then cooled, diluted with iced water, neutralised by addition of a solution of 2N NaOH and extracted with ether.

The combined organic solutions are washed with water, dried over $Na_2SO_4$ and evaporated. The solid residue is taken up in ether and is added to a solution of H Cl in ether.

Crystals of dihydrochloride are obtained, melting point 238°–240° (yield, 90%).

Many other derivative corresponding to the formula(I) have been prepared by the process according to the invention, for example:

2-β-hydroxyphenethylamino 5-(N-diethylaminoethylidene) Δ²-thiazoline(yield 40%; melting point: 129°–131° C (derivative No. 4); $R_1$ = β-hydroxy phenethyl; $R_2$ = H; $R_3$ = $R_4$ = ethyl.

2-N-diethylamino 5-(N-cyclohexyl N-methyl-aminoethylidene) Δ²-thiazoline dioxalate (yield 33%); melting point: 170°–172° C (derivative No. 5); $R_1$ = $R_2$ = ethyl; $R_3$ = cyclohexyl; $R_4$ = methyl.

2-cyclohexylamino 5-(N-cyclohexyl N-methylaminoethylidene) Δ²-thiazoline (yield 74%); melting point: 113°–115° C (derivative No. 6); $R_1$ = $R_3$ = cyclohexyl; $R_2$ = H; $R_4$ = methyl.

2-amino 5-β-N-diethylaminoethylidene Δ²-thiazoline dihydrochloride (yield 12%); melting point: 210° C (derivative No. 7). $R_1$ = $R_2$ = H; $R_3$ = $R_4$ = ethyl.

2-cyclohexylamino 5-β-morpholinoethylidene Δ²-thiazoline (yield 73%); melting point: 144°–146° C (derivative No. 8) $R_1$ = cylohexyl; $R_2$ = H; $N(R_3R_4)$ = morpholino.

2-butylamino 5-β-diethylaminoethyl thiazole dihydrochloride (yield 55%); melting point; 188°–190° C (derivative No. 9) $R_1$ = normal butyl; $R_2$ = H; $R_3$ = $R_4$ = ethyl.

5-(β-diethylaminoethylidene) 2-N-ethyl N-cyclohexylamino) Δ²-thiazoline oxalate (yield 43%); melting point: 138°–140° C (derivative No. 10) $R_1$ = $R_3$ = $R_4$ = ethyl; $R_2$ = cyclohexyl.

5-(β-diethylaminoethylidene) 2-(N-methyl N-cyclohexylamino) Δ²-thiazoline dioxalate (yield 52%); melting point: 172°–174° C) (derivative No. 11) $R_1$ = methyl; $R_2$ = cyclohexyl; $R_3$ = $R_4$ = ethyl.

5-(2-diethylamino ethylidene) 2-(4-methyl 1-piperazinyl) Δ²-thiazoline tetrahydrochloride (yield 23%); melting point: 220° C (derivative No. 12) $N(R_1R_2)$ = 4-methyl piperazinyl; $R_3$ = $R_4$ = ethyl.

2-cyclohexylamino 5-(β-piperidyl ethlidene) Δ²-thiazoline (yield 76%); melting point 134°–136° C (derivative No. 13). $R_1$ = cyclohexyl; $R_2$ = H; $N(R_3R_4)$ = piperidino 5-β-diethylaminoethylidene 2-morpholino $\Delta^2$-thiazoline oxalate (yield 49%); melting point 170°–172° C (derivative No. 14) $N(R_1R_2)$ = morpholino; $R_3 = R_4$ = ethyl.

2-diethylamino 5-(2-diethylamino ethylidene) $\Delta^2$-thiazoline dioxalate (yield 43%); melting point: 134°–135° C (derivative No. 15) $R_1 = R_2 = R_3 = R_4$ = ethyl.

5-(2-dimethylamino ethylidene)2-ethylamino $\Delta^2$-thiazoline oxalate (yield 35%); melting point: 145° C (derivative No. 16) ;$R_1$ = H; $R_2$ = ethyl; $R_3 = R_4$ = methyl.

2-butylamino 5-(2-diethylamino ethylidene) $\Delta^2$-thiazoline dihydrochloride (yield 52%) melting point; 190°–194° C (derivative No. 17) $R_1$ = n-butyl; $R_2$ = H; $R_3 = R_4$ = ethyl.

5-(β-diethylamino ethylidene) 2-(1,1,3,3-tetramethyl-butyl-amino) $\Delta^2$-thiazoline (yield 39%); melting point: 200° C (derivative No. 18) $R_1$ = 1,1,3,3-tetramethyl-butyl; $R_2$ = H; $R_3 = R_4$ = ethyl.

2-ethylamino 5-[2(1-pyrrolidinyl)ethylidene] $\Delta^2$-thiazoline (yield 45%); melting point 84°–86° C (derivative No. 19) $R_1$ = ethyl; $R_2$ = H; $N(R_3R_4)$ = pyrrolidinyl.

2-cyclohexylamino 5-[2-(1pyrrolidinyl)ethylidene] $\Delta^2$-thiazoline (yield 64%); melting point 133°–134° C (derivative No. 20) $R_1$ = cyclohexyl; $R_2$ = H; $N(R_3R_4)$pyrrolidinyl 5-(β-diethylaminoethylidene) 2-methylamino $\Delta^2$-thiazoline oxalate (yield 50%); melting point 178°–180° C (derivative No. 21) $R_1$ = methyl; $R_2$ = H; $R_3 = R_4$ = ethyl.

5-β-diethylaminoethyl 2-(N-methyl N-cyclohexylamino)-thiazole dioxalate (yield 70%); melting point: 80° C (derivative No. 22); $R_1$ = methyl; $R_2$ = cyclohexyl; $R_3 = R_4$ = ethyl.

2-benzylamino 5-β-diethylaminoethylidene $\Delta^2$-thiazoline dihydrochloride (yield 63%); melting point 235° C (derivative No. 23). $R_1$ = benzyl; $R_2$ = H; $R_3 = R_4$ = ethyl.

5-(β-diethylaminoethylidene) 2-isopropylamino $\Delta^2$-thiazoline dioxalate (yield 46%); melting point: 164°–166° C (derivative No. 24) $R_1$ = H; $R_2$ = isopropyl; $R_3 = R_4$ = ethyl.

2-(4-chlorobenzylamino) 5-β-diethylaminoethylidene $\Delta^2$-thiazoline dihydrochloride (yield 35%); melting point: 210°–220° C (derivative No. 25) $R_1$ = H; $R_2$ = (4-chlorobenzyl); $R_3 = R_4$ = ethyl.

2-cyclopentylamino 5-β-diethylaminoethylidene $\Delta^2$-thiazoline (yield 47%); melting point: 89°–90° C (derivative No. 26); $R_1$ = H; $R_2$ = cyclopentyl; $R_3 = R_4$ = ethyl.

2-cyclo-octylamino 5-β-diethylaminoethylidene $\Delta^2$-thiazoline (yield 46%); melting point: 70° C (derivative No. 27); $R_1$ = H; $R_2$ = cyclo-octyl; $R_3 = R_4$ ethyl.

2-cycloheptylamino 5-β-diethylaminoethylidene $\Delta^2$-thiazoline (yield 44%); melting point 92° C (derivative No. 28); $R_1$ = H; $R_2$ = cycloheptyl; $R_3 = R_4$ = ethyl.

2-cyclododecylamino 5-β-diethylaminoethylidene $\Delta^2$-thiazoline (yield 50%); melting point: 93° C (derivative No. 29); $R_1$ = H; $R_2$ = cyclodoecyl; $R_3 = R_4$ = ethyl.

2-allylamino 5-β-diethylaminoethylidene $\Delta^2$-thiazoline dihydrochloride (yield 31%); melting point: 190° C (derivative No. 30); $R_1$ = H; $R_2$ = allyl; $R_3 = R_4$ = ethyl.

2-dicyclohexylamino 5-β-diethylaminoethylidene $\Delta^2$-thiazoline oxalate (yield 40%); melting point: 210° C (derivative No. 31); $R_1 = R_2$ = cyclohexyl; $R_3 = R_4$ = ethyl.

The results of the toxicological and pharmacological tests reported hereinafter show clearly the interesting activity of the compounds according to the invention, notably their hypocholesterolemic and anti-inflammatory activity.

I. TOXICOLOGICAL STUDY

This study has clearly shown the low toxicity of the derivatives of the invention.

By way of example, the $LD_{50}/24$ h/kg of body weight measured by the method of Miller & Tainter, by the intravenous route, is, in mice, 90mg for derivative No. 12; 45 mg for derivative No. 18; 105 mg for derivative No. 14; 92 mg for derivative No. 21, and 42 mg for derivative No. 1.

During the tests for acute, chronic, or retarded toxicity, excellent tolerance has been shown to compounds of the invention; they have caused no difficulty, no local or general reaction and no disturbance in the test animals.

II. PHARMACOLIGICAL STUDY

1. Hypocholesterolemic action a. Propyl-thiouracil test (RANNEY et Coll. J. Pharmacol. Exper. Therap. 1963, 142, 132–136)

The administration of propyl-thiouracil to adult rats renders them hypercholesterolemic; in effect, the plasmatic cholesterol rate has increased by about 15%. The testing is carried out on two groups of rats, the control group receiving the propyl-thiouracil only whilst the treated group also receives 100 mg/kg of the compounds to be tested, by the oral route.

On the 11th day of the experiment, the blood samples are taken and the β-lipoproteins, the free cholesterol and the total cholesterol measured. The results show that in the treated animals, the rate of free cholesterol and total cholesterol are clearly reduced. The results obtained for some of the compounds are summarised in the following table:

|  | Free Cholesterol g/l | Total Cholesterol g/l |
|---|---|---|
| Control Sample | 0.20 | 0.86 |
| Derivative No 1 | 0.14 | 0.60 |
| Derivative No 9 | 0.15 | 0.58 |
| Derivative No 12 | 0.15 | 0.61 |
| Derivative No 15 | 0.12 | 0.58 | b. Triton test

The intravenous injection of Triton W-R 1339 (an alkylaryl polyetheralcohol sold by by Rohm and Haas) enables one to artifically increase, in the rat, certain lipidic fractions of serum and thus to evalute the hypocholesterolemic action of the compounds of the invention.

These are administered by the oral route in a dose of 100 mg/kg immediately after the intravenous injection of the Triton.

Eighteen hours later a blood sample is taken and the β-lipoproteins, the free cholesterol and the cholesterol are determined. As in the preceding test, significantly low amounts of free cholesterol and of total cholesterol are found, of the order of 28% for derivative No. 1, 24% for derivative No. 9, 26% for derivative No. 12 and 22% for derivative No. 15.

2. Anti-inflammatory action a. Localised carrageenin-induced oedema method

A 1% solution of carrageenin (0.1 ml) is injected into the metatarsal flexor muscles of the right hand rear paw of the rat at time "0".

The animals of the treated group also receive, by the oral route, 100 mg/kg of the compound to be tested, respectively 1 hour before and at the same time as the injection of the phlogogenic agent, then 1 hour and 2½ hours after. The measurements made with the aid of a micrometer at the time "0" and 1 hour, 2 hours, 3 hours and 5 hours after the administration of the carrageenin, enable one to determine, in relation to time, the percentage of anti-inflammatory activity in relation to the control group. The results are summarised in the following table:

| Products | First Hour | Second Hour | Third Hour | Fifth Hour |
| --- | --- | --- | --- | --- |
| Derivative No 3 | 37 | 39 | 46 | 48 |
| Derivative No 4 | 39 | 40 | 49 | 53 |
| Derivative No 10 | 44 | 47 | 52 | 56 |
| Derivative No 22 | 42 | 46 | 54 | 56 | b. Generalised ovalbumin-induced oedema method

A simultaneous intraperitoneal injection of 1 ml of ovalbumin and of 0.5 ml of an aqueous solution of Evans Blue at 1 ml per thousand by weight is administered to rats.

For comparative purposes, 100 mg of the compound to be tested is administered orally to the animals of the group to be treated, 1 hour before and at the same time as the ovalbumin. The intensity of the phenomenon thus provoked in noted by a FIG. 1 to 5 according to the intensity of the inflammatory syndrome.

Thus one determines the average of the oedematic intensity and the percentage of decrease of the oedematic reaction in relation to the control animals. The results are summarised in the following table:

| Products | Second Hour | Third Hour |
| --- | --- | --- |
| Derivative No 3 | 54 | 60 |
| Derivative No 4 | 59 | 65 |
| Derivative No 10 | 57 | 64 |
| Derivative No 22 | 52 | 60 |

The toxicological and pharmacological studies which have just been reported show that the compounds of the invention are well tolerated by the test animals and that they possess hypocholesterolemic and anti-inflammatory activities.

It will be appreciated from the above that the compounds of the invention and their non-toxic salts may be used to advantage in medicine.

By regulating the metabolism of the cholesterol and of the body lipids, they can successfully protect the body from vascular attacks of atherosclerosic origin, and from the cardiac, cerebral and peripheral complications thereof.

Moreover they intervene effectively in the inflammatory reaction, thus reducing or preventing oedema, hypersecretion, and exudation.

They are recommendable for the treatment of hypercholesterolemia and hyperlipidemia and the complications thereof, chronic inflammatory rheumatism, degenerative rheumatism, abarticular afflictions, for acute and sub-acute otorhinolaryngological inflammations, in reparative surgery and plastic surgery and in functional re-education.

For this purpose, the compounds of the invention may be formulated for oral administration in the form of tablets, coated tablets, capsules, drops, or syrups.

They may also be formulated for rectal administration in the form of suppositories and for parenteral administration in the form of an injectable solution.

In these formulations, the active principle is associated with an excipient or a solid carrier or a sterile and/or flavoured liquid, in dosage units form, the active principle being present in an amount of from 0.01% to 80% by weight of the composition.

Each dosage unit advantageously contains from 0.05 g to 0.500 g of active principle, the daily dose varying from 0.050 g to 1.50 g according to the severity of the condition being treated and the age of the patient.

There will be given hereinafter, by way of example, some pharmaceutical formulations of the compounds of the invention.

| 1 TABLETS | |
| --- | --- |
| Derivative No. 1 | 0.100 g |
| Lactose | 0.010 g |
| Methyl cellulose | 0.005 g |
| Tartrazine | Trace |
| Microcrystalline cellulose | 0.010 g |
| Corn starch | 0.025 g |
| Magnesium stearate | 0.010 g |

| 2 — COATED TABLETS | |
| --- | --- |
| Core: | |
| Derivative No. 12 | 0.100 g |
| Lactose | 0.015 g |
| Corn starch | 0.005 g |
| Magnesium stearate | 0.005 g |
| Coating: | |
| Gum-lac | 0.001 g |
| Gum arabic | 0.005 g |
| Talc | 0.010 g |
| Carnauba wax | 0.003 g |
| Orange, codex "S" | Trace |
| White sugar | sufficient to make one coated tablet. |

| 3 — CAPSULES | |
| --- | --- |
| Derivative No. 3 | 0.150 g |
| Corn starch | 0.020 g |
| Magnesium stearate | 0.010 g |

| 4 — SYRUP | |
| --- | --- |
| Derivative No. 22 | 2 g |
| Excipient | 100 ml |

| 5 — INJECTABLE SOLUTION | |
| --- | --- |
| Derivative No. 15 | 0.100 g |
| Isotonic solution | sufficient to make 5 ml |

| 6 — SUPPOSITORIES | |
| --- | --- |
| Derivative No. 9 | 0.150 g |
| Semi-synthetic triglycerides | sufficient to make one suppository. |

As regards the isothiocyanates used to prepare the compounds of the invention, that N which $R_3=R_4=$ ethyl has a melting point of 103° C at 0.3 mm of mercury.

Other examples of compounds of the invention are:
5-diethylaminoethyl 2-cyclododecylamino thiazole (yield 55%) -m.p. 100°–120° C. (Derivative No. 32); $R_1 = H$, $R_2 =$ cyclododecyl; $R_3 = R_4 =$ ethyl.

2-cyclododecylamino 5-(N-benzyl N-ethylaminoethylidene) $\Delta^2$-thiazolidine (yield 62%) m.p. 77° C (derivative No. 33); $R_1 = H$, $R_2 =$ cyclododecyl; $R_3 =$ benzyl; $R_4 =$ ethyl.

EXAMPLE 34

Preparation of 5-[4-β-(parachlorophenyl) piperazino ethylidene] 2-cyclohexylamino $\Delta^2$-thiazoline - (derivative No. 34) $R_1 =$ cyclohexyl; $R_2 =$ H.

Into a mixture of 5 g (0.019 mole) of 1-amino (4-parachlorophenyl) 4-piperazino 2-butyne and 50 ml of chloroform is introduced, dropwise, a solution of 2.68g (0.019 mole) of cyclohexylisothiocyanate in 50 ml of chloroform.

The mixture is stirred for 2 hours at ambient temperature, then the solvent is evaporated. The residue is taken up in 65 ml of 2N HCl then heated for 1 hour under reflux. After cooling, the solution is neutralised by addition of a solution of 2N NaOH. The precipitate formed is filtered, washed with water, dried, and then recrystallised from a cyclohexane/benzene mixture.

Crystals are collected (yield 44%) whose melting point, determined by Koefler block, is 180° C.

The following compounds have been prepared by the same method:

2-cyclohexylamino 5-[4-β-(phenyl) piperazinoethylidene] $\Delta^2$-thiazoline (derivative No. 35); yield 52% — melting point 145° C. $R_1=$cyclohexyl; $R_2 =$ H;

2-cyclohexylamino 5-[4-β-metatrifluoromethyl) piperazino ethylidene] $\Delta^2$-thiazoline (derivative No. 36) — yield 47%, melting point 192° C. $R_1 =$ cyclohexyl; $R_2 =$ H;

5-[4-β-(orthochlorophenyl) piperazinoethylidene]2-cyclohexylamino $\Delta^2$-thiazoline (derivative No. 37) — yield 58% — melting point 175° C. $R_1$ cyclohexyl; $R_2 =$ H; and 2-cyclohexylamino 5-[4-β-(paramethoxyphenyl) piperazinoethylidene] $\Delta^2$-thiazoline (derivative No. 38); yield 47% — melting point 160° C; $R_1 =$ cyclohexyl; $R_2 =$ H.

III. TOXICOLOGICAL STUDY

The derivative Nos. 34 to 38 have been shown to be very well tolerated in all our tests and they have not given rise to any undesirable secondary reaction at therapeutic doses.

By way of example, the $LD_{50}/24$ hours /kg of body weight determined by the method of Miller & Tainter, by the intravenous route, is 35 mg for derivative No. 34, 48 mg for derivative No. 35, 65 mg for derivative No. 36, 57 mg for derivative No. 37 and 52 mg for derivative No. 38.

IV. PHARMACOLOGICAL STUDY

1. Hypocholesterolemic action a. Propyl-thiouracil test (Ranney et Coll. J. Pharmacol. Exper. Therap. 1963, 142, 132–136)

This test has shown the clearly favourable action of the derivatives according to the invention, at a dose of 50 mg/kg.

The results are summarised in the following table:

|  | Free cholesterol | Total cholesterol |
| --- | --- | --- |
| Control | 0.25 | 0.89 |
| Derivative No. 34 | 0.13 | 0.55 |
| Derivative No. 35 | 0.11 | 0.61 |
| Derivative No. 36 | 0.13 | 0.63 |
| Derivative No. 37 | 0.10 | 0.60 |
| Derivative No. 38 | 0.9 | 0.58 | b. Triton test

This test, which enables one to evaluate the hypocholesterolemic action of the derivatives to be tested, on serum levels of certain lipid fractions, has shown the remarkable effect of the compounds according to the invention. Our tests have shown that the levels of free cholesterol and total cholesterol are considerably reduced in the animals treated with oral doses of 50 mg/kg of the compounds according to the invention.

These reductions are of the order of 34% for derivative No. 34; of 29% for derivative No. 35; of 27% for derivative No. 36; of 41% for derivative No. 37; and 44% for derivative No. 38.

2. Anti-inflammatory reaction a. method of localised carrageenin-induced oedema.

The oral administration of 50 mg/kg of the derivatives to be tested produces a clear reduction of the inflammatory reaction provoked.

The results are summarised in the following table:

| Products | 1st hour | 2nd hour | 3rd hour | 4th hour | 5th hour |
| --- | --- | --- | --- | --- | --- |
| Derivative No. 34 | 40 | 44 | 50 | 53 | 55 |
| Derivative No. 35 | 45 | 46 | 55 | 57 | 58 |
| Derivative No. 36 | 46 | 50 | 59. | 61 | 62 |
| Derivative No. 37 | 38 | 43 | 48 | 52 | 57 |
| Derivative No. 38 | 49 | 53 | 56 | 60 | 61 | b. method of generalised ovalbumin-induced oedema

The percentages of reduction of oedematic reaction, in the test animals, in subjects treated by the oral route by the administration of 50 mg/kg of the compound to be tested show the clear anti-inflammatory action of the compounds according to the invention.

| Products | 1st hour | 2nd hour |
| --- | --- | --- |
| Derivative No. 34 | 58 | 62 |
| Derivative No. 35 | 62 | 65 |
| Derivative No. 36 | 55 | 61 |

-continued

| Products | 1st hour | 2nd hour |
| --- | --- | --- |
| Derivative No. 37 | 60 | 68 |
| Derivative No. 38 | 64 | 70 |

What I claim is:

1. A thiazoline of the formula:

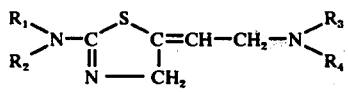

wherein $R_1$ and $R_2$ are each selected from hydrogen, alkenyl having 1–12 carbon atoms, alkyl having 1–12 carbon atoms, cycloalkyl having 4–12 carbon atoms, phenyl, cycloalkylphenyl wherein the cycloalkyl moiety has 4–12 carbon atoms, phenylalkyl wherein the alkyl moiety has 1–12 carbon atoms, halogencycloalkyl having 4–12 carbon atoms, halogenphenyl, halogenoalkyl having 1–12 carbon atoms and the same monosubstituted by a hydroxy, with the proviso that at least one of $R_1$ and $R_2$ is cyclic, $R_3$ and $R_4$ are each independently selected from hydrogen and alkyl having 1–12 carbon atoms, and their pharmaceutically acceptable acid addition salts.

2. The thiazoline of claim 1 wherein $R_1$ and $R_2$ are each independently selected from hydrogen, methyl, ethyl, butyl, hydroxyphenethyl, benzyl, chlorobenzyl and cycloalkyl.

3. The thiazoline of claim 1 wherein $R_3$ and $R_4$ are each independently selected from hydrogen, methyl, and ethyl.

4. The thiazoline of claim 1 wherein $R_1$ is cycloalkyl.

5. The thiazoline of claim 4 wherein $R_1$ is selected from cyclopentyl, cyclohexyl, cyclohepthyl, cyclooctyl and cyclododecyl.

6. 2-cyclohexylamino-5-$\beta$-diethylaminoethylidene$\Delta^2$-thiazoline.

* * * * *